United States Patent [19]

Hamashima et al.

[11] 4,066,641
[45] Jan. 3, 1978

[54] METHOD FOR CYCLIZATION TO GIVE CEPHEM RING

[76] Inventors: Yoshio Hamashima, 26-20, Katsurahitsuji-saru-cho,, Ukyo, Kyoto, Kyoto; Mitsuru Yoshioka, 2-5-A9-102, Shinsenri-higashi, Toyonaka, Osaka; Hiroshi Tanida, 1-5-9, Mandai, Abeno, Osaka, Osaka; Teruji Tsuji, 1-14-9, Yanagawa-cho, Takatsuki, Osaka; Masayuki Narisada, 3-24-5, Ayukawa, Ibaraki, Osaka; Taichiro Komeno, 2-6-23, Nishisuminoe, Suminoe, Osaka, Osaka; Wataru Nagata, 6-10, Kawahigashi-cho, Nishinomiya, Hyogo, all of Japan

[21] Appl. No.: 707,288

[22] Filed: July 21, 1976

[30] Foreign Application Priority Data

July 22, 1975 Japan .................................. 50-89915

[51] Int. Cl.² .......................................... C07D 501/02
[52] U.S. Cl. ...................... 544/17; 424/246; 260/239 A; 260/239.1; 544/26; 544/27; 544/28; 544/22; 544/30; 544/29; 544/16
[58] Field of Search ..................................... 260/243 C

[56] References Cited
U.S. PATENT DOCUMENTS 3,944,545   3/1976   Chou ................. 260/243 C

*Primary Examiner*—Nicholas S. Rizzo
*Attorney, Agent, or Firm*—Wenderoth, Lind & Ponack

[57] ABSTRACT

A compound represented by

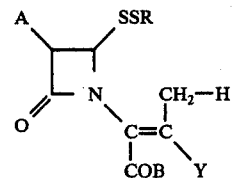

is treated with a base to give an antibacterial cephem compound represented by

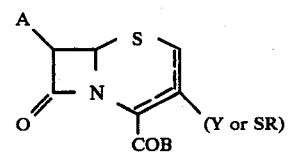

(wherein
A is amino or substituted amino;
COB is carboxy or protected carboxy;
RS is substituted thio;
Y is an electron-attracting group selected from acyloxy, halogen, cyano, nitro, and nitroso; and
the dotted line shows $\Delta^2$ or $\Delta^3$).

8 Claims, No Drawings

METHOD FOR CYCLIZATION TO GIVE CEPHEM RING

I. SCOPE

This invention relates to a cyclization process to give a cephem ring represented by the following reaction scheme:

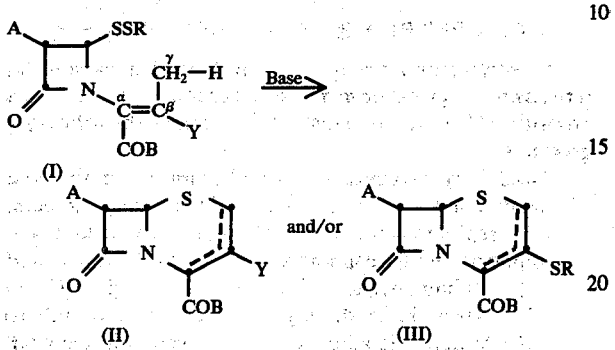

(wherein
- A is amino or substituted amino;
- COB is carboxy or protected carboxy;
- RS is substituted thio;
- Y is an electron-attracting group selected from acyloxy, halogen, cyano, nitro, and nitroso; and
- the dotted line shows 2- or 3-double bond).

No cyclization of β-methyl compounds (I) to give cephems (II) and/or (III) is known. The starting compound (I) is producible from penicillins by known methods.

1. SUBSTITUTED AMINO A

The substituted amino A can be a side chain of natural or synthetic penicillins and cephalosporins stable during said cyclization. It can be organic or inorganic acylamino, acylimido, hydrocarbylamino, sulfenylamino, silylamino, or an acid addition salt at the amino.

Representative acyl groups for A can be selected from the following groups:

1. ($C_1$ to $C_{10}$)alkanoyl;
2. ($C_1$ to $C_5$)haloalkanoyl;
3. azidoacetyl or cyanoacetyl;
4. acyl groups represented by formula:

Ar—CQQ'—CO—

[in which Q and Q' each is hydrogen or methyl and Ar is phenyl, dihydrophenyl, or monocyclic hetero aromatic group containing from 1 to 4 hetero ring atoms selected from N, O, and/or S atoms, and each can optionally be substituted by an inert group (e.g. ($C_1$ to $C_5$)alkyl, trifluoromethyl, cyano, aminomethyl, optionally protected carboxymethylthio, hydroxy, ($C_1$ to $C_3$)alkoxy, ($C_1$ to $C_{10}$)acyloxy, chlorine, bromine, iodine, fluorine, nitro)];

5. 2-sydnon-3-acetyl or (4-pyridon-1-yl)acetyl;
6. acyl groups represented by formula:

Ar—G—CQQ'—CO—

(in which Ar, Q, and Q' are as defined above and G is O or S atom);

7. acyl groups represented by formula:

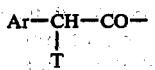

(in which Ar is as defined above and T is
   i. hydroxy or ($C_1$ to $C_{10}$)acyloxy;
   ii. carboxy, ($C_2$ to $C_7$)alkoxycarbonyl, ($C_2$ to $C_{15}$)aralkoxycarbonyl, ($C_1$ to $C_{12}$)aryloxycarbonyl, ($C_1$ to $C_7$)alkanoyloxy($C_1$ to $C_3$)alkoxycarbonyl, cyano, or carbamoyl;
   iii. sulfo or ($C_1$ to $C_7$)alkoxysulfonyl);

8. acyl groups represented by formula:

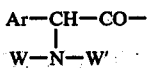

[in which Ar is as defined above and W and W' each is hydrogen or a substituent (e.g. ($C_2$ to $C_7$)-alkoxycarbonyl, ($C_3$ to $C_{10}$)cycloalkyl($C_2$ to $C_3$)alkoxycarbonyl, ($C_5$ to $C_8$)cycloalkoxycarbonyl, ($C_1$ to $C_4$)alkylsulfonyl-($C_1$ to $C_4$)-alkoxycarbonyl, halo($C_1$ to $C_3$)alkoxycarbonyl, ($C_1$ to $C_{15}$)aralkoxycarbonyl, ($C_1$ to $C_{10}$)alkanoyl, or ($C_2$ to $C_{15}$)aroyl, each optionally substituted by an inert group (e.g. hydroxy, ($C_1$ to $C_{10}$)alkanoyloxy, halogen, ($C_1$ to $C_5$)alkyl, ($C_1$ to $C_3$)hydroxyalkyl, trifluoromethyl), pyronecarbonyl, thiopyronecarbonyl, pyridonecarbonyl, carbamoyl, guanidinocarbonyl, optionally substituted ureidocarbonyl (e.g. 3-methyl-2-oxoimidazolidin-1-ylcarbonyl, 3-methanesulfonyl-2-oxoimidazolidin-1-ylcarbonyl), optionally substituted aminooxalylcarbamoyl (e.g. 4-methyl-2,3-dioxopiperazin-1-ylcarbonyl, 4-ethyl2,3-dioxopiperazin-1-ylcarbonyl), optionally substituted thioureidocarbonyl equivalents of above ureidocarbonyl, or W, W' and the nitrogen atom combined together represent phthalimido, maleimido, or enamino derived from enolizable carbonyl compound (e.g. ($C_5$ to $C_{10}$)acetoacetates, ($C_4$ to $C_{10}$)acetacetamides, acetylacetone, acetoacetonitrile, 1,3-cyclopentanedione)];

9. acyl groups represented by formula:

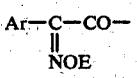

(in which Ar is as defined above and E is hydrogen or ($C_1$ to $C_5$)alkyl);

10. 5-aminoadipoyl, N-protected 5-aminoadipoyl (protected by e.g. ($C_1$ to $C_{10}$)alkanoyl, ($C_1$ to $C_{10}$)aralkanoyl, ($C_2$ to $C_{11}$)aroyl, ($C_1$ to $C_5$)haloalkanoyl, or ($C_2$ to $C_{10}$)alkoxycarbonyl); or carboxyprotected 5-aminoadipoyl (protected by e.g. ($C_1$ to $C_5$)alkyl, ($C_2$ to $C_{21}$)aralkyl, or ($C_1$ to $C_{10}$)aryl), each protecting group can optionally be sutstituted by ($C_1$ to $C_5$)alkyl, ($C_1$ to $C_5$)alkoxy, halogen, or nitro); and 11. acyl groups represented by formula:

L—O—CO—

[in which L is an easily removable and optionally substituted ($C_1$ to $C_{10}$)hydrocarbyl group (e.g. t-butyl, 1,1-dimethylpropyl, cyclopropylmethyl, 1-methylcyclohexyl, isobornyl, 2-alkoxy-t-butyl, 2,2,2-trichloroethyl, benzyl, naphthyl, p-methoxybenzyl, pyridylmethyl, diphenylmethyl)].

Alternatively, A can be a diacylimido group derived from ($C_4$ to $C_{10}$)polybasic carboxylic acids.

Another substituted amino for A includes optionally substituted ($C_1$ to $C_{20}$)hydrocarbyl or hydrocarbylidene (e.g. methyl, ethyl, propyl, t-butyl, trityl, methylidene, benzylidene, 1-halo-2-phenylethylidene, 1-alkoxy-2-phenylethylidene, 3,5-dit-butyl-4-hydroxybenzylidene, o-hydroxybenzylidene), and ($C_2$ to $C_{10}$)organic silyl (e.g. trimethylsilyl).

A group convertible into amino or amido (e.g. azido, isocyanato, isocyano) is another member of A.

Two amino substituents in A can combine to form a ring.

Reactive A can be protected and afterwards deprotected by conventional methods.

Most preferable A includes phenoxyacetamido and phenylacetamido.

2. CARBOXY-PROTECTING GROUP B

The group COB can be a protected carboxy (e.g. in forms of ester, amide, acid halide, acid anhydride, and salt groups).

From another aspect, the group B can be an oxygen function [for example ($C_1$ to $C_{10}$)alkoxy e.g. methoxy, ethoxy, t-butoxy; ($C_7$ to $C_{20}$)aralkoxy (e.g. benzyloxy, methoxybenzyloxy, nitrobenzyloxy, diphenylmethoxy, trityloxy); ($C_5$ to $C_{15}$)aryloxy (e.g. phenoxy, naphthyloxy); ($C_1$ to $C_{12}$)organometaloxy (e.g. trimethylstannyl oxy, dimethylchlorosilyloxy, trimethylsilyloxy); ($C_1$ to $C_{15}$)organic or inorganic acyloxy; metaloxy of the group I, II, or III in the periodical table (e.g. sodiooxy, potassiooxy, magnesiooxy); or ($C_1$ to $C_{12}$)ammonium oxy]; sulfur function [for example that forming e.g. ($C_1$ to $C_{12}$)thiol ester, thiocarboxy, or like groups], nitrogen function [forming e.g. amides (e.g. N-($C_1$ to $C_5$)alkylamide, N,N-di($C_1$ to $C_5$)alkylamide, amide with imidazole or phthalimide); hydrazide, azide, or like nitrogen functions]; or halogen atom (e.g. chlorine or bromine).

These groups can, where possible, have a hetero atom selected from O, N, and/or S atoms in their skeleton, or can be unsaturated or substituted by a substituent (e.g. nitrogen, oxygen, sulfur, carbon, or phosphorous functions, halogen atoms).

Typical examples of COB group include those forming ($C_1$ to $C_5$)haloalkyl esters, ($C_2$ to $C_5$)acylalkyl esters, ($C_5$ to $C_8$)aryl esters, ($C_5$ to $C_{20}$)aralkyl esters, esters with ($C_1$ to $C_{12}$)oxim, ($C_1$ to $C_5$)N-alkoxyamides, imides with dibasic acid, N,N'-hi($C_3$ to $C_5$)alkylhydrazide, alkali metal or alkaline earch metal salts, ($C_1$ to $C_5$)alkylamine salts, and groups equivalent in effect to those groups. (In above paragraph, specified numbers of carbon atom are these for B).

Preferable COB is carboxylic ester group (especially methyl, t-butyl, 2,2,2-trichloroethyl, methanesulfonylethyl, pivaloyloxymethyl, phenacyl, benzyl, p-methoxybenzyl, p-nitrobenzyl, benzhydryl, indanyl, benzaldoxime, N,N-dimethylaminoethyl, and trimethylsilyl esters), and alkali metal or alkaline earth metal salt, (especially lithium, sodium, potassium, magnesium, and other equivalent salt groups).

3. SUBSTITUTED THIO GROUP RS

The substituted thio group RS can be 1) ($C_1$ to $C_{15}$)arylthio (e.g. phenylthio, 2- or 4-nitrophenylthio, 2,4-dinitrophenylthio, 4-cyano-2-nitrophenylthio, 6-chloro-2-nitrophenylthio, imidazol-2-ylthio, thiazol-2-ylthio, 2-methyl-1,3,4-thiadiazol-5-ylthio, oxazol-2-ylthio, 1,3,4-oxadiazol-2-ylthio, 1-methyltetrazol-5-ylthio, 2-pyridylthio, 2-quinolylthio, 1-methylbenzimidazol-2-ylthio, benzothiazol-2-ylthio, benzoxazol2-ylthio, and the like arylthio groups, each can optionally be substituted by ($C_1$ to $C_5$)alkyl, cyano, carboxy, ($C_1$ to $C_5$acyloxy($C_1$ to $C_5$)alkyl, trifluoromethyl ($C_1$ to $C_5$)alkoxy, ($C_1$ to $C_{12}$)acyloxy, halogen, nitro, or like substituents), 2) aralkylthio (e.g. benzylthio, α-carbethoxybenzylthio), 3) acylthio (e.g. ($C_1$ to $C_{12}$)alkanoylthio, aroylthio), or other substituted thio leaving group.

More preferable RS includes benzothiazol-2-ylthio, thiazol-2-ylthio, acetylthio, and o-nitrophenylthio.

4. ELECTRON-ATTRACTING GROUP Y

The electron-attracting group Y is that capable of releasing a proton from the γ-carbon atom. Y has a positive Hammett σ-constant. Y includes the following groups:

1. acyloxy or acylthio derived from e.g. carboxylic acid, sulfonic acid, sulfinic acid, phosphonic acid, phosphinic acid, carbonic acid, sulfuric acid, phosphoric acid, phosphorous acid, or halogen acid (including straight, branched, or cyclic ($C_1$ to $C_{12}$)alkanoic acid, ($C_2$ to $C_{12}$)aroic acid, ($C_2$ to $C_{12}$)aralkanoic acid, ($C_1$ to $C_{12}$)alkanesulfonic acid, ($C_1$ to $C_{12}$)arylsulfonic acid, di($C_1$ to $C_5$)alkylphosphonic acid, di($C_1$ to $C_7$)arylphosphonic acid, straight, branched, or alicyclic ($C_1$ to $C_{12}$)alkoxyformic acid, dialkylphosphoric acid).

Typical acyloxy include ($C_1$ to $C_5$)alkanoyloxy, ($C_1$ to $C_5$)alkoxycarbonyloxy, ($C_7$ to $C_{12}$)aralkoxycarbonyloxy, ($C_6$ to $C_{11}$)aroyloxy, ($C_1$ to $C_5$)alkanesulfonyloxy, and ($C_6$ to $C_8$)arylsulfonyloxy;

2. cyano, thiocyanato, nitro, nitroso; and 3. halogen (e.g. chlorine, bromine, iodine).

II. STARTING MATERIALS

The starting materials (I) can be prepared by conventional methods by 1) treating a penicillin sulfoxide ester with a thiol RSH, 2) subjecting the products to ozonolysis, and then 3) introducing the group Y to the formed oxo compound, as is summarized in the following reaction scheme:

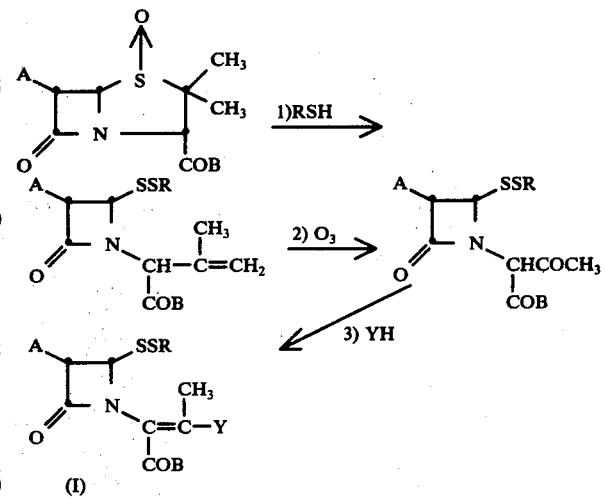

(wherein A, COB, RS, and Y are as defined above).

III. STATE OF ART

After the priority date of this application, German Patent Application (OLS) No. 2,506,330 was opened to the public. The processes described therein resemble the instant process, but 1) Y is an electron-donating group (e.g. ether-forming alkoxy, aralkoxy, and silyloxy) in contrast to the instant electron-attracting group (e.g. acyloxy, halogen, etc.) and 2) the base is mainly 1,5-diazabicyclo[5,4,0]undec-5-ene in the German case.

IV. PROCESS

In the process of this invention, the starting material (I) is treated with a base. Said base includes those which eliminate a proton from γ-carbon atom (e.g. tertiary amines and secondary amines).

Illustratives of such bases are ($C_1$ to $C_{15}$)tertiary amines (e.g. trimethylamine, triethylamine, tripropylamine, butyldimethylamine, 1-methylpiperidine, N-methylmorpholine, quinuclidine, 4-piperidylpyridine, 1,2,2,6,6-pentamethylpiperidine, 1,4-diazabicyclo[2,2,2]octane); ($C_5$ to $C_{15}$)aromatic substituted tertiary amines (e.g. N,N-dimethylaniline, 1,8-bisdimethylaminonaphthalene, and the like); bulky secondary bases (e.g. diisopropylamine); and other rather weak bases.

The reaction can be carried out under the following conditions:
1. at −60° C to 40° C;
2. under anhydrous condition and/or in an inert gas; and
3. in a solvent (e.g. hydrocarbon, halohydrocarbon, ester, ether, ketone, amide, alcohol, and nitrile solvents). Preferable solvents are lower alkanols, tetrahydrofuran, dioxane, ether, dimethylformamide, dimethylacetamide, hexamethylphosphorotriamide, benzene, toluene, xylene, and mixtures thereof.

V. PRODUCTS

When Y is strongly electron-attractive (e.g. halogen, sulfonyloxy), the group SR migrates to position β of compounds (I) or position 3 on the cephem ring accompanied by elimination of Y to produce the cephems (III) and YH.

When Y is weakly electron-attractive, RS leaves from the molecule of compound (I) upon cyclization to give cephems (II) and RSH.

When Y is moderately electron-attractive, both cephems (II) and (III) are formed simultaneously.

The cephems (II) and (III) have a double bond on their cephem ring primarily at position 3, but the double bond tends to migrate giving partly or mainly 2-cephems. If required, sulfoxide formation and subsequent reduction give 3-cephems in pure state.

The cephems (II) and (III) can be isolated and purified by conventional methods (e.g. chromatography, precipitation, extraction, recrystallization, absorption, and solution).

VI. USE

Now known or unknown cephems (II) and (III) are antibacterials and/or intermediates for producing cephalosporins by conventional methods.

For example, when 3-substituent is acyloxy, 7-side chain is replaced by amino with phosphorous pentachloride and methanol and acylated to give protected phenylglycinamido side chain; 3-acyloxy is hydrolyzed with a base and substituted by methoxy with diazomethane or by chlorine with oxalyl chloride; and then the protecting group at the side chain and position 4 is removed to give 7β-phenylglycinamido-3-(methoxy or chloro)-3-cephem-4-carboxylic acid for oral use.

Similarly, when 3-substituent is hetero aromatic thio, 7-side chain is replaced by amino with phosphorous pentachloride and butanol and acylated to give phenylacetamido side chain; and then 4-carboxy is liberated to give 7β-phenylacetamido3-hetero aromatic thio-3-cephem-4-carboxylic acid, which can be treated with sodium lactate to give injectable sodium salt.

The antibacterial cephems (II) and (III) can be administered to patients at a daily dose of e.g. 0.5 to 3 g per man for prevention or treatment of bacterial infections caused by sensitive bacteria as solutions, tablets, capsules, or like conventional pharmaceutical forms, if required with e.g. water, calcium carbonate, starch, or like conventional excipients.

VII. TERMS

The specific terms used in the specification and claims can represent the following meanings unless otherwise specified:

Alkyl: Straight, branched, or cyclic ($C_1$ to $C_{12}$)alkyl optionally possessing a substituent as defined below. For example, the alkyl include methyl, ethyl, propyl, isopropyl, n-butyl, s-butyl, t-butyl, cyclopropylmethyl, pentyl, isoamyl, cyclopentylmethyl, n-hexyl, 2-methylpentyl, cyclohexyl, n-heptyl, isooctyl, n-nonyl, n-decyl, cyclohexylbutyl, ethylcyclopentylpropyl, and cycloheptyl.

The definition is applicable to alkoxy, alkylthio, alkylamino (including dialkylamino), aralkyl (including diarylalkyl), and other groups containing an alkyl moiety.

Aryl: A (mono or di)cyclic and (carbo or hetero)-aromatic group containing up to 10 carbon atoms in the skeleton optionally possessing a substituent defined below. The hetero aromatic group can possess hetero atom selected from O, N, and/or S atoms. For example, the aryl includes monocyclic ones e.g. furyl, thienyl, pyrryl, oxazolyl, isoxazolyl, oxadiazolyl, oxatriazolyl, thiazolyl, isothiazolyl, thiadiazolyl, thiatriazolyl, pyrazolyl, imidazolyl, triazolyl, tetrazolyl, pyridyl, pyrimidyl, pyrazinyl, pyridazinyl, triazinyl, phenyl; and bicyclic ones e.g. naphthyl, quinolyl, isoquinolyl, benzopyrimidyl, benzothienyl, benzothiazolyl, benzoisoxazolyl, benzotriazolyl, indenyl, pyrimidopyrimidyl, and pyridopyridyl.

The definition is applicable to aryloxy, arylthio, arylamino, (including diarylamino), aralkyl(inclduing diarylalkyl and triarylalkyl), aroyl, aralkanoyl(including diaralkanoyl), and other groups containing an aryl moiety.

Acyl: An acyl derived from ($C_1$ to $C_{20}$)organic or inorganic acids including aliphatic, araliphatic, aromatic, or mineral acids (belonging to e.g. carboxylic, sulfonic, sulfinic, phosphonic, carbonic, carbamic, nitric, sulfuric, phosphoric, halogenic, or hydrohalogenic acids).

The definition is applicable to acyloxy, acylthio, acylamino (including diacylamino), and other groups containing an acyl moiety.

Substituent: S substituent means a group linking through carbon, nitrogen, sulfur, or oxygen atoms, or halogen atom.

Typical examples of them include
1. Carbon function e.g. alkyl, aralkyl, aryl, acyl, carboxy, carboxyalkyl, acyloxyalkyl, hydroxyalkyl, mercaptoalkyl, aminoalkyl, acylaminoalkyl, cyano;
2. Oxygen function e.g. hydroxy, alkoxy, acyloxy, aryloxy, aralkyloxy, oxo;

3. Sulfur function e.g. mercapto, sulfo, sulfonyl, sulfinyl, alkylthio, aralkylthio, arylthio, acylthio;
4. Nitrogen function e.g. amino, alkylamino, acylamino, aralkylamino, arylamino, nitro, hydrazo; and
5. Halogen.

Protection of functional groups

When the groups A, B, and R have a reactive moiety, it can be protected with suitable protecting groups which are endurable in chemical reactions or utilization as drugs. Such groups can be introduced or removed by conventional protection or deprotection procedures well known in the art.

The following Examples are given to show more detailed embodiment of this invention, but they are not given to restrict the scope thereof.

EXAMPLE 1

To a solution of 2,2,2-trichloroethyl α-[4-(benzothiazol-2-yl)dithio-3-phenoxyacetamido-2-oxoazetidin-1-yl]-α-(1-cyclopropylmethoxycarbonyloxyethylidene)acetate (374 mg) in N,N-dimethylformamide (8 ml) is added thiethylamine (0.35 ml) at −20° C, and the mixture is kept at −20° C to −10° C for 5.5 hours. The reaction mixture is poured into 5% phosphoric acid aqueous solution and extracted with ethyl acetate. The extract is washed with water, dried, and chromatographed over silica gel containing 10% water to give 2,2,2-trichloroethyl 3-cyclopropylmethoxycarbonyloxy-7-phenoxyacetamido-3-cephem-4-carboxylate (80 mg). Yield: 27%.

EXAMPLE 2

The product of Example 1 can also be prepared by treating the same starting material with diisopropylamine (0.4 ml) in place of triethylamine in Example 1 at −10° C for 1.5 hours.

EXAMPLE 3

In a procedure similar to that of Example 1, p-nitrobenzyl α-[4-(benzothiazol-2-yl)dithio-3-phenoxyacetamido-2-oxoazetidin-1-yl]-α-(1-cyclopropylmethoxycarbonyloxyethylidene)acetate (515 mg) is treated with triethylamine (330 mg) in N,N-dimethylformamide (10 ml) at −20° C for 3 hours to give the starting material (115 mg) and a mixture of p-nitrobenzyl 3-cyclopropylmethoxycarbonyloxy-7-phenoxyacetamido-2- and -3-cephem-4-carboxylate (20 mg).

EXAMPLE 4

To a solution of 2,2,2-trichloroethyl α-[4-(benzothiazol-2-yl)dithio-3-phenoxyacetamido-2-oxoazetidin-1-yl]-α-(1-acetoxyethylidene)acetate (344 mg) in N,N-dimethylformamide (10 ml) is added triethylamine under cooling at −30° C, and the mixture is stirred for 3 hours at −20° C to 0° C. The reaction mixture is poured into 5% phosphoric acid aqueous solution and extracted with ethyl acetate. The extract is washed with water, dried, and evaporated. The resulting residue is chromatographed over silica gel containing 10% water to give a mixture of 2,2,2-trichloroethyl 3-acetoxy-7-phenoxyacetamido-2- and -3-cephem-4-carboxylate (66 mg, ca. 2:1). Yield: 25.2%.

EXAMPLE 5

In a procedure similar to that of Example 4, 2,2,2-trichloroethyl α-[4-(benzothiazol-2-yl)dithio-3-phenylacetamido-2-oxoazetidin-1-yl]-α-(1-acetoxyethylidene)acetate (300 mg) is treated with triethylamine (200 mg) in N,N-dimethylformamide (10 ml) at −30° C for 5 hours to give 2,2,2-trichloroethyl 3-acetoxy-7-phenylacetamido-3-cephem-4-carboxylate (38 mg, Yield: 17%) and the starting material (Recovery: 49%).

EXAMPLE 6

In a procedure similar to that of Example 4, 2,2,2-trichloroethyl α-[4-(benzothiazol-2-yl)dithio-3-phenylacetamido-2-oxoazetidin-1-yl]-α-(1-isopropionyloxyethylidene)acetate (384 mg) is treated with triethylamine (270 mg) in N,N-dimethylformamide (10 ml) at −20° C to −10° C for 6 hours to give 2,2,2-trichloroethyl 3-isopropionyloxy-7-phenylacetamido-3-cephem4-carboxylate (51 mg, Yield: 17%) and the starting material (Recovery: 20%).

EXAMPLE 7

To a solution of 2,2,2-trichloroethyl α-[4-(benzothiazol-2-yl)dithio-3-phenylacetamido-2-oxoazetidin-1-yl]-α-(1-diethylphosphoroyloxyethylidene)acetate (312 mg) in N,N-dimethylformamide (6 ml) is added triethylamine (0.28 ml) at −20° C, and the mixture is stirred for 5 hours. The reaction mixture is poured into ice-water and extracted with ethyl acetate. The extract solution is washed with water, dried, and evaporated. The obtained residue is chromatographed over silica gel containing 10% water to give a mixture of 2,2,2-trichloroethyl 3-diethylphosphoroyloxy-7-phenylacetamido-2- and -3-cephem-4-carboxylate (84 mg, Yield: 34.4%).

EXAMPLE 8

In a procedure similar to that of Example 7, 2,2,2-trichloroethyl α-[4-(benzothiazol-2-yl)dithio-3-phenoxyacetamido-2-oxoazetidin-1-yl]-α-(1-diethylphosphoroyloxyethylidene)acetate (183 mg) is treated with triethylamine (160 mg) in N,N-dimethylformamide (8 ml) at −20° C for 3 hours to give a mixture of 2,2,2-trichloroethyl 3-diethylphosphoroyloxy-7-phenoxyacetamido-2- and -3-cephem-4-carboxylate (58 mg, 1:1). Yield: 40.8%.

EXAMPLE 9

In a procedure similar to that of Example 7, 2,2,2-trichloroethyl α-[4-(benzothiazol-2-yl)dithio-3-phenoxyacetamido-2-oxoazetidin-1-yl]-α-(1-p-nitrobenzoyloxyethylidene)acetate (160 mg) is treated with triethylamine (150 mg) in N,N-dimethylformamide (7 ml) at −20° C for 2 hours to give a mixture of 2,2,2-trichloroethyl 3-p-nitrobenzoyloxy-7-phenoxyacetamido-2- and -3-cephem-4-carboxylate (28 mg). Yield: 22%.

IR: $\nu_{max}^{CHCl_3}$ 1792, 1697, 1640, 1150 cm$^{-1}$.

Physical constants of the compounds prepared in Examples 1 to 8 are shown in Table I.

EXAMPLE 10

To a solution of 2,2,2-trichloroethyl α-[4-(benzothiazol-2-yl)dithio-3-phenoxyacetamido-2-oxoazetidin-1-yl]-α-(1-chloroethylidene)acetate (200 mg) in methanol (20 ml) is added triethylamine (50 mg), and the reaction mixture is kept at room temperature for 1.75 hours. The reaction mixture is poured into 5% phosphoric acid aqueous solution and extracted with ethyl acetate. The extract is washed with water, dried, and evaporated to dryness under reduced pressure. The obtained residue is chromatographed over silica gel to give methyl 3-(benzothiazol-2-yl)thio-7-phenoxyacetamido-2-cephem-4-carboxylate (42 mg). (Ester exchange occured to give methyl ester from 2,2,2-trichloroethyl ester).

EXAMPLE 11

The product of Example 10 can also be prepared by treating with diisopropylamine (50 mg) in place of triethylamine in the procedure of Example 10.

EXAMPLE 12

In a procedure similar to that of Example 10, 2,2,2-trichloroethyl α-[2β-(4-benzothiazol-2-yl)dithio-3-phenoxyacetamido-2-oxoazetidin-1-yl]-α-(1-chloroethylidene)acetate (164 mg) is treated with triethylamine (130 mg) in N,N-dimethylformamide (5 ml) at −30° C to −35° C for 1.5 hours to give 2,2,2-trichloroethyl 3-(benzothiazol-2-yl)thio-7-phenylacetamido-2-cephem-4-carboxylate (49 mg).

EXAMPLE 13

To a solution of 2,2,2-trichloroethyl α-[4-(benzothiazol-2-yl)dithio-3-phenoxyacetamido-2-oxoazetidin-1-yl]-α-(1-chloroethylidene)acetate (1000 mg) in N,N-dimethylformamide (30 ml) is added triethylamine (800 mg) at −30° C to −35° C, and the mixture is stirred for 2.25 hours at the same temperature. The reaction mixture is poured into 5% phosphoric acid aqueous solution and extracted with ethyl acetate. The extract solution is washed with water, dried, and evaporated. The obtained residue is chromatographed over silica gel to separate the product as an oil (856 mg).

A part of the obtained product (300 mg) is re-chromatographed over silica gel to give 2,2,2-trichloroethyl 3-(benzothiazol-2-yl)thio-7-phenoxyacetamido-2-cephem-4-carboxylate (173 mg) and 2,2,2-trichloroethyl 3-(benzothiazol-2-yl)thio-7-phenoxyacetamido-3-cephem-4-carboxylate (17 mg).

EXAMPLE 14

To a solution of p-nitrobenzyl α-[4-(benzothiazol-2-yl)dithio-3-phenylacetamido-2-oxoazetidin-1-yl]-α-(1-methanesulfonyloxyethylidene)acetate (10.5 g) in N,N-dimethylformamide (300 ml) is added triethylamine (11.6 ml) at −40° C, and the mixture is stirred at −35° C for 2 hours. The reaction mixture is poured into 5% phosphoric acid aqueous solution (100 ml), diluted with water, and extracted with ethyl acetate. The extract solution is washed with water, dried, and evaporated. The obtained residue (9.43 g) is chromatographed over silica gel to separate p-nitrobenzyl 3-(benzothiazol-2-yl)thio-7-phenylacetamido-3-cephem-4-carboxylate (336 mg) and p-nitrobenzyl 3-(benzothiazol-2-yl)thio-7-phenylacetamido-2-cephem-4-carboxylate (1.63 g).

EXAMPLE 15

In a procedure similar to that of Example 14, 2,2,2-trichloroethyl α[4-(benzothiazol-2-yl)dithio-3-phenoxyacetamido-2-oxoazetidin-1-yl]-α-(1-toluene-p-sulfonyloxyethylidene)acetate (332 mg) is treated with triethylamine (200 mg) in N,N-dimethylformamide (10 ml) at −45° C to −30° C giving 2,2,2-trichloroethyl 3-(benzothiazol-2-yl)thio-7-phenoxyacetamido-2- and -3-cephem-4-carboxylate.

EXAMPLE 16

1. To a solution of 2,2,2-trichloroethyl α-(4-acetyldithio-3-phenoxyacetamido-2-oxoazetidin-1-yl)-α-(1-hydroxyethylidene)acetate (166 mg) in N,N-dimethylformamide (2 ml) is added oxalyl chloride (100 μl) under ice-cooling, and the mixture is stirred for 3 hours at room temperature. The reaction mixture is poured into ice-water and extracted with ethyl acetate. The extract solution is washed with water, dried, and evaporated. The obtained residue (135 mg) is chromatographed over silica gel (3 g) and eluted with ethyl acetate-benzene mixture (1:10) to give 2,2,2-trichloroethyl α-(4-acetyldithio-3-phenoxyacetamido-2-oxoazetidin-1-yl)-α-(1-chloroethylidene)acetate (70 mg) as oil.

IR: $\nu_{max}^{CHCl_3}$ 3435, 1786, 1740, 1710, 1705 cm$^{-1}$.
NMR: $\delta^{CDCl_3}$ 1.97s+2.13s(4:1)3H, 2.55s+2.72s(4:1)3H, 4.58s2H, 4.87m2H, 5.22q+5.65q(4:1)(5;8Hz)1H, 6.15d(5Hz)1H, 6.87–7.40m6H.

2. To a solution of 2,2,2-trichloroethyl α-(4-acetyldithio-3-phenoxyacetamido-2-oxoazetidin-1-yl) -α-(1-chloroethylidene)acetate (115 mg) in N,N-dimethylformamide (1 ml) is added triethylamine (140 μl) at −60° C, and the mixture is stirred for 3 hours. The reaction mixture is kept at 0° C, poured into 5% phosphoric acid aqueous solution, and extracted with ethyl acetate. The extract solution is washed with water, dried, and evaporated. The obtained residue (87 mg) is chromatographed over silica gel (1.5 g) and eluted with ethyl acetate-benzene (1:10) mixture to give 2,2,2-trichloroethyl 3-acetylthio-7-phenoxyacetamido-2- and -3-cephem-4-carboxylate (5 mg, Δ$^2$ : Δ$^3$ = ca. 2:1).

EXAMPLE 17

1. To a solution of 2,2,2-trichloroethyl α-[4-(thiazol-2-yl)dithio-3-phenylacetamido-2-oxoazetidin-1-yl]-α-(1-hydroxyethylidene)acetate (275 mg) in N,N-dimethylformamide (3 ml) is added dropwise oxalyl chloride (100 mg) under ice cooling, and the mixture is kept at room temperature overnight. Then, the mixture is poured into ice-water and extracted with ethyl acetate. The extract solution is washed with water, dried, and evaporated. The obtained residue (270 mg) is chromatographed over silica gel (5 g) and eluted with ethyl acetate-benzene (1:10) mixture to give 2,2,2-trichloroethyl α-[4-(thiazol-2-yl)dithio-3-phenylacetamido-2-oxoazetidin-1-yl]-α-(1-chloroethylidene)acetate (90 mg) as a (2:1) mixture of geometrical isomers at ethylidene group.

IR: $\nu_{max}^{CHCl_3}$ 3430, 1785, 1745, 1676, 1141 cm$^{-1}$.
NMR: $\delta^{CDCl_3}$ 2.60s+2.70s(2:1)3H, 3.70s2H, 4.73s+4.82s(1:2)2H, 4.93–5.07m1H, 5.78d(5Hz)1 H, 6.43–6.70d1H, 7.37br–s6H, 7.70d(3Hz)1H.

2. To a solution of 2,2,2-trichloroethyl α-[4-(thiazol-2-yl)dithio-3-phenylacetamido-2-oxoazetidin-1-yl]-α-(1-chloroethylidene)acetate (42 mg) in N,N-dimethylformamide (1 ml) is added triethylamine (60 μl) at −40° C, and the mixture is stirred at −40° C for 30 minutes and at −20° C to −10° C for 3.5 hours. The mixture is poured into 5% phosphoric acid aqueous solution and diluted with water. The separated precipitate (25 mg) is collected by filtration, and chromatographed over silica gel (1 g) using ethyl acetate-benzene (1:10) mixture to give oily 2,2,2-trichloroethyl 3-(thiazol-2-yl)thio-7-phenylacetamido-2-cephem-4-carboxylate (14 mg).

Physical constants of the compounds produced in Examples 10–17 are shown in Table II.

TABLE I

[Structure: β-lactam with A-CH-S-CH=C(Y)-COOX ring system]

| Compound No. | A | X | Y | Δ | IR:ν$_{max}^{CHCl_3}$(cm$^{-1}$) | NMR:δ$^{CDCl_3}$ ( ) means coupling constant Hz |
|---|---|---|---|---|---|---|
| 1 | $C_6H_5OCH_2CONH-$ | $-CH_2CCl_3$ | $-OCOCH_2-\triangleleft$ | 3 | 3420,1795, 1765,1693. | 0.06–1.43m5H,3.60q(18)2H,4.56s2H,4.86d(8) 2H,4.90s2H,5.12d(5)1H,5.97dd(5;9)1H, 6.77–7.53m6H. |
| 2 | $C_6H_5OCH_2CONH-$ | $-CH_2CCl_3$ | $-OCH_3$, $-OC_2H_5$ ($-OP$) | 3. | — | 2.25s3H3.57ABq(19)2H,4.60s2H, 4.86ABq(9)2H,5,10d(5)1H,6.00dd(5;9)1H, 6.67–7.63m5H. |
| 3 | $C_6H_5OCH_2CONH-$ | $-CH_2CCl_3$ | $-OCH_3$, $-OC_2H_5$ ($-OP$) | 2+3 (1:1) | 3430,1795 1695,1675, 1260,1023. | 1.35t(7)6H,3.58ABq(2;20)2H,3.90–4.62m3H, 4.55s2H,6.32dd(2;2)1H,6.67–7.63m6H. |
| 4 | $C_6H_5OCH_2CONH-$ | $-CH_2-\bigcirc-NO_2$ | $-OCOCH_2-\triangleleft$ | 2+3 (1:1) | — | 0.26–1.60m5H,3.53ABq(18)2H,3.93d(7)2H, 4.50s2H,5.03d(4)1H,5.27br-s2H,5.83dd (4;9)1H,6.27s1H,6.63–8.20m9H. |
| 5 | $C_6H_5CH_2CONH-$ | $-CH_2CCl_3$ | $-OCCH$, $CH_3$, $CH_3$ | 3 | — | 1.23d(6)6H,2.6m1H,3.47ABq(18)2H,3.63s2H, 4.80ABq(11)2H,5.05d(5)1H,5.82dd(5;8)1H, 6.53d(8)1H,7.3s5H. |
| 6 | $C_6H_5CH_2CONH-$ | $-CH_2CCl_3$ | $-OCCH_3$ | 3 | — | 2.23s3H,3.47ABq(18)2H,3.63s2H,4.83s2H, 5.03d(5)1H,5.82d(5;8)1H,6.82d(8)1H, 7.3s5H. |
| 7 | $C_6H_5CH_2CONH-$ | $-CH_2CCl_3$ | $-OCH_3$, $-OC_2H_5$ ($-OP$) | 2+3 (1:2) | 3440,1790, 1695,1269, 1028. | 1.33t(7)6H,3.60s2H,3.67m2H,3.80–4.52m 4H,4.73ABq(13)2H,6.23dd(2;2)1H,6.68d (9)1H,7.25s5H. |

TABLE II

Structure: A-[β-lactam with S ring]-N-C(=O), with SR and COOX substituents

| Compound No. | A | X | SR | Δ | IR:$\nu_{max}^{CHCl_3}(cm^{-1})$ | NMR: $\delta CDCl_3$ ( ) means coupling constant Hz |
|---|---|---|---|---|---|---|
| 1 | C₆H₅OCH₂CONH— | —CH₃ | benzothiazol-2-yl-S— | 2 | 3425,1784, 1743,1692, 1598. | 3.66s3H,4.58s2H,5.40d(1.5)1H, 5.42d(5)1H,5.73dd(5;8)1H, 6.8–8.0,11H. |
| 2 | C₆H₅OCH₂CONH— | —CH₂CCl₃ | benzothiazol-2-yl-S— | 2 | 3455,1790, 1770,1700. | 4.56s2H,4.73s2H,5.43d(4)1H, 5.60d(1)1H,5.75dd(4;8)1H, 6.8–8.0m11H |
| 3 | C₆H₅OCH₂CONH— | —CH₂CCl₃ | benzothiazol-2-yl-S— | 3 | 3425,1795, 1750,1695, 1600. | 3.73ABq(18)2H,4.50s2H,4.87q(12)2H, 5.12d(5)1H,5.95dd(5;9)1H,6.70–8.05m10H. |
| 4 | C₆H₅OCH₂CONH— | —CH₂CCl₃ | —SCOCH₃ | 2+3(2:1) | 3425,1792 1770,1682, 1150. | 2.32s3H,3.48s,4.58s2H,4.78s2H, 4.87–5.87m3H,6.80d(2), 6.90–7.67m6H. |
| 5 | C₆H₅CH₂CONH— | —CH₂CCl₃ | thiazol-2-yl-S— | 2 | 3430,1793, 1690. | 3.63s2H,4.68s2H,5.33d(4)1H, 5.50d(2)1H,5.77dd(4;8)1H, 7.0–7.9m10H. |
| 6 | C₆H₅CH₂CONH— | —CH₂CCl₃ | benzothiazol-2-yl-S— | 2 | 3425,1790, 1765,1680, 1147. | 3.63s2H,4.72s2H,5.30d(4)1H,5.32d(2)1H, 5.63dd(4;8)1H,6.58d(8.5)1H,7.02d(2)1H, 7.25d(3)1H,7.32s5H,7.65d(3)1H. |
| 7 | C₆H₅CH₂CONH— | —CH₂-C₆H₄-NO₂ | benzothiazol-2-yl-S— | 2 | 3380,1780, 1730,1680, 1350. | 3.90ABq(18)2H,5.35d(5)1H,5.45s2H 5.90dd(5;8)1H,7.28s5H,7.25–8.08m7H. |
| 8 | C₆H₅CH₂CONH— | —CH₂-C₆H₄-NO₂ | benzothiazol-2-yl-S— | 3 | 3380,1790, 1740,1680, 1350. | 3.67s2H,5.12s2H,5.22d(4,5)1H,5.28d(2)1H, 5.65dd(4.5)1H,6.67d(8)1H,7.12d(2)1H, 7.28s5H,7.29–8.15m7H. |

(m.p. 202–204° C)

What we claim is:

1. A process for preparing a compound of the formula

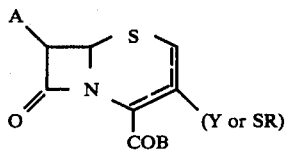

wherein A is amino, sulfenylamino or amino substituted by (1) $C_1$ to $C_{10}$ alkanoyl, (2) $C_1$ to $C_5$ haloalkanoyl, (3) azidoacetyl, (4) cyanoacetyl, (5) acyl of the formula Ar—CQQ'—CO— in which each of Q and Q' is hydrogen or methyl and Ar is phenyl, dihydrophenyl or a monocyclic hetero aromatic group containing 1–4 hetero ring atoms selected from the group consisting of nitrogen, oxygen and sulfur, (6) 2-sydnon-3-acetyl, (7) (4-pyridon-1-yl)acetyl, (8) acyl of the formula Ar—G—CQQ'—CO— in which Ar, Q and Q' are as defined above and G is oxygen or sulfur, (9) acyl of the formula

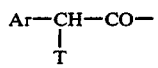

in which Ar is as defined above and T is hydroxy, $C_1$ to $C_{10}$ acyloxy, carboxy, $C_2$ to $C_7$ alkoxycarbonyl, $C_2$ to $C_{15}$ aralkoxycarbonyl, $C_1$ to $C_{12}$ aryloxycarbonyl, $C_1$ to $C_7$ alkanoyloxy-$C_1$ to $C_3$ alkoxycarbonyl, cyano, carbamoyl, sulfo or $C_1$ to $C_7$ alkoxysulfonyl, (10) acyl of the formula

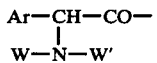

in which Ar is as defined above and each of W and W' is hydrogen, $C_2$ to $C_7$ alkoxycarbonyl, $C_3$ to $C_{10}$ cycloalkyl-$C_2$ to $C_3$ alkoxycarbonyl, $C_5$ to $C_8$ cycloalkoxycarbonyl, $C_1$ to $C_4$ alkylsulfonyl-$C_1$ to $C_4$ alkoxycarbonyl, halo $C_1$ to $C_3$ alkoxycarbonyl, $C_1$ to $C_{15}$ aralkoxycarbonyl, $C_1$ to $C_{10}$ alkanoyl, $C_2$ to $C_{15}$ aroyl, pyronecarbonyl, thiopyronecarbonyl, pyridonecarbonyl, carbamoyl, guanidinocarbonyl, 3-methyl-2-oxoimidazolidin-1-ylcarbonyl, 3-methanesulfonyl-2-oxoimidazolidin-1-ylcarbonyl, 4-methyl-2,3-dioxopiperazin-1-ylcarbonyl, or 4-ethyl-2,3-dioxopiperazin-1-ylcarbonyl, or W and W' are combined together with the nitrogen atom to which they are attached to form phthalimido, maleimido or enamino derived from $C_5$ to $C_{10}$ acetoacetate, $C_4$ to $C_{10}$ acetacetamide, acetylacetone, acetoacetonitrile or 1,3-cyclopentanedione, (11) acyl of the formula

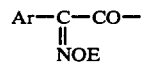

in which Ar is as defined above and E is hydrogen or $C_1$ to $C_5$ alkyl, (12) 5-aminoadipoyl, N-protected 5-aminoadipoyl wherein the protecting group is $C_1$ to $C_{10}$ alkanoyl, $C_1$ to $C_{10}$ aralkanoyl, $C_2$ to $C_{11}$ aroyl, $C_1$ to $C_5$ haloalkanoyl or $C_2$ to $C_{10}$ alkoxycarbonyl, or carboxyprotected 5-aminoadipoyl wherein the protecting group is $C_1$ to $C_5$ alkyl, $C_2$ to $C_{21}$ aralkyl or $C_1$ to $C_{10}$ aryl, (13) acyl of the formula L-O-CO- in which L is $C_1$ to $C_{10}$ hydrocarbyl, (14) diacylimido derived from a $C_4$ to $C_{10}$ polybasic carboxylic acid, (15) $C_1$ to $C_{20}$ hydrocarbyl, (16) $C_1$ to $C_{20}$ hydrocarbylidene, (17) $C_2$ to $C_{10}$ organic silyl, (18) azido, (19) isocyanato, or (20) isocyano, COB is a carboxylic ester group, RS is benzothiazol-2-ylthio, thiazol-2-ylthio or acetylthio, Y is $C_1$ to $C_5$ alkanoyloxy, $C_1$ to $C_5$ alkoxycarbonyloxy, $C_7$ to $C_{12}$ aralkoxycarbonyloxy, $C_6$ to $C_{11}$ aroyloxy, $C_1$ to $C_5$ alkanesulfonyloxy, $C_6$ to $C_8$ arylsulfonyloxy, cyano, thiocyanato, nitro, nitroso, chlorine, bromine or iodine, and the dotted line represents a 2- or 3- double bond, which comprises reacting a compound of the formula

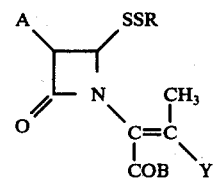

wherein A, COB, RS and Y have the same meanings as above, with a base selected from the group consisting of trimethylamine, triethylamine, tripropylamine, butyldimethylamine, 1-methylpiperdine, N-methylmorpholine, quinuclidine, 4-piperidylpyridine, 1,2,2,6,6-pentamethylpiperidine, 1,4-diazabicyclo[2,2,2]octane, N,N-dimethylaniline, 1,8-bisdimethylaminonaphthalene and diisopropylamine.

2. A process according to claim 1, wherein RS is benzothiazol-2-ylthio or thiazol-2-ylthio.

3. A process according to claim 1, wherein the reaction is carried out in a solvent selected from the group consisting of a hydrocarbon, a halohydrocarbon, an ester, an ether, a ketone, an amide, an alcohol, a nitrile and a mixture thereof.

4. A process according to claim 1, wherein the reaction product is a compound of the formula

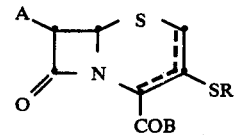

wherein A, COB, RS, and the dotted line are as defined above.

5. A process according to claim 1, wherein A is phenylacetamido or phenoxyacetamido.

6. A process according to claim 1, wherein RS is benzothiazol-2-ylthio, thiazol-2-ylthio, or acetylthio.

7. A process according to claim 1, wherein the reaction is carried out at −60° C to 40° C.

8. A process according to claim 1, wherein the reaction is carried out under anhydrous condition and/or in an inert gas.

* * * * *